(12) United States Patent
Shahpasand (10) Patent No.: US 10,570,195 B2
(45) Date of Patent: Feb. 25, 2020

(54) CONFORMATION-INDEPENDENT ANTIBODIES AGAINST NEUROTOXIC TAU PROTEINS

(71) Applicant: Koorosh Shahpasand, Tehran (IR)

(72) Inventor: Koorosh Shahpasand, Tehran (IR)

( * ) Notice: Subject to any disclaimer, the term of this patent is extended or adjusted under 35 U.S.C. 154(b) by 0 days.

(21) Appl. No.: 16/297,815

(22) Filed: Mar. 11, 2019

(65) Prior Publication Data

US 2019/0211087 A1   Jul. 11, 2019

Related U.S. Application Data

(60) Provisional application No. 62/641,357, filed on Mar. 11, 2018.

(51) Int. Cl.
*C07K 16/18* (2006.01)
*G01N 33/68* (2006.01)

(52) U.S. Cl.
CPC ......... *C07K 16/18* (2013.01); *G01N 33/6896* (2013.01); *C07K 2317/24* (2013.01); *C07K 2317/565* (2013.01); *C07K 2317/622* (2013.01); *G01N 2800/2821* (2013.01)

(58) Field of Classification Search
None
See application file for complete search history.

(56) References Cited

U.S. PATENT DOCUMENTS

| 8,940,272 | B2 * | 1/2015 | Nitsch | C07K 16/18 424/1.49 |
| 9,186,423 | B1 * | 11/2015 | Lin | A61K 51/04 |
| 9,598,484 | B2 * | 3/2017 | Weinreb | C07K 16/18 |
| 9,688,747 | B2 * | 6/2017 | Lu | C07K 16/18 |
| 9,810,691 | B2 * | 11/2017 | Bresalier | G01N 33/57419 |
| 2006/0166283 | A1 * | 7/2006 | Delacourte | C07K 16/40 435/7.2 |
| 2009/0068691 | A1 * | 3/2009 | Dave | G01N 33/6893 435/7.92 |
| 2010/0278803 | A1 * | 11/2010 | Zhao | G01N 33/6896 424/94.6 |
| 2013/0028900 | A1 | 1/2013 | Lu et al. | |
| 2015/0050215 | A1 | 2/2015 | Novak et al. | |
| 2017/0198349 | A1 * | 7/2017 | Rice | C12Q 1/6883 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*

* cited by examiner

*Primary Examiner* — Adam Weidner
(74) *Attorney, Agent, or Firm* — Bajwa IP Law Firm; Haris Zaheer Bajwa (57) ABSTRACT

An antibody or fragment thereof capable of binding to a neurotoxic tau protein. The neurotoxic tau protein includes a phosphorylation site at threonine residue 231 in AT180 domain of tau proteins and an amino acid substitution of proline residue 232 to glycine (P232G) in AT180 domain of tau proteins.

15 Claims, 10 Drawing Sheets

Specification includes a Sequence Listing.

| Name | Live cells | Dead cells |
|---|---|---|
| Healthy neurons |  |  |
| Alzheimer's disease (AD) neurons |  |  |
| AD neurons treated with the exemplary antibody |  |  |

SEQUENCE LISTING

```
<160> NUMBER OF SEQ ID NOS: 8

<210> SEQ ID NO 1
<211> LENGTH: 960
<212> TYPE: DNA
<213> ORGANISM: Artificial Sequence
<220> FEATURE:
<223> OTHER INFORMATION: Synthetic sequence

<400> SEQUENCE: 1
tggtgcaatt ctatttcagg agacagtcat aatgaaatac ctattgccta cggcagccgc      60
tggattgtta ttactcgcgg cccagccggc catggccgag gtgcagctgt tggagtctgg     120
gggaggcttg gtacagcctg gggggtccct gagactctcc tgtgcagcct ctggattcac     180
ctttagcagc tatgccatga gctgggtccg ccaggctcca gggaaggggc tggagtaggt     240
ctcaagtatt aataattctg gttcttatac atattacgca gactccgtga agggccggtt     300
caccatctcc agagacaatt ccaagaacac gctgtatctg caaatgaaca gcctgagagc     360
cgaggacacg gccgtatatt actgtgcgaa agctgattat tcttttgact actggggcca     420
gggaaccctg gtcaccgtct cgagcggtgg aggcggttca ggcggaggtg gcagcggcgg     480
tggcgggtcg acggacatcc agatgaccca gtctccatcc tccctgtctg catctgtagg     540
agacagagtc accatcactt gccgggcaag tcagagcatt agcagctatt taaattggta     600
tcagcagaaa ccagggaaag cccctaagct cctgatctat gctgcatcct ctttgcaaag     660
tggggtccca tcaaggttca gtggcagtgg atctgggaca gatttcactc tcaccatcag     720
cagtctgcaa cctgaagatt ttgcaactta ctactgtcaa cagaatactg ctgatcctga     780
tacgttcggc caagggacca aggtggaaat caaacgggcg gccgcacatc atcatcacca     840
tcacggggcc gcagaacaaa aactcatctc agaagaggat ctgaatgggg ccgcatagac     900
tggtgaaart gtttagcaaa cctcatacag aaattcattt actacgtctg gaaagacgac     960

<210> SEQ ID NO 2
<211> LENGTH: 8
<212> TYPE: PRT
<213> ORGANISM: Artificial Sequence
<220> FEATURE:
<223> OTHER INFORMATION: Synthetic sequence

<400> SEQUENCE: 2

Gly Phe Thr Phe Ser Ser Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic sequence

<400> SEQUENCE: 3

Ile Gly Asn Asp Gly Thr Asn Thr
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic sequence

<400> SEQUENCE: 4

Ala Lys Asn Ala Tyr Ser Phe Asp Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic sequence

<400> SEQUENCE: 5

Gln Ser Ile Ser Ser Tyr
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic sequence

<400> SEQUENCE: 6

Asn Ala Ser Gly
1

<210> SEQ ID NO 7
<211> LENGTH: 9
<212> TYPE: PRT
<213> ORGANISM: Artificial Sequence
<220> FEATURE:
<223> OTHER INFORMATION: Synthetic sequence

<400> SEQUENCE: 7

Gln Gln Ser Asp Thr Ser Pro Thr Thr
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (6)..(6)
<223> OTHER INFORMATION: PHOSPHORYLATION

<400> SEQUENCE: 8

Val Ala Val Val Arg Thr Gly Pro Lys Ser Pro
1               5                   10
```

CONFORMATION-INDEPENDENT ANTIBODIES AGAINST NEUROTOXIC TAU PROTEINS

CROSS-REFERENCE TO RELATED APPLICATION

This application claims the benefit of priority from pending U.S. Provisional Patent Application Ser. No. 62/641,357, filed on Mar. 11, 2018, and entitled "METHODS AND COMPOSITIONS FOR THE GENERATION AND USE OF CONFORMATION-INDEPENDENT ANTIBODIES AGAINST PT231-TAU DOMAIN," which is incorporated herein by reference in its entirety.

TECHNICAL FIELD

The present disclosure generally relates to therapeutic and diagnostic antibodies and their fragments that bind to neurotoxic tau proteins, particularly to conformation-independent antibodies against phosphorylated Tau proteins, and more particularly to a method for using the exemplary antibodies and their fragments for diagnosing tauopathy disorders.

BACKGROUND

Alzheimer's disease (AD) is the sixth leading cause of death globally in which abnormal phosphorylation of tau proteins may be the most pathological hallmark. Tau proteins are phosphoproteins which may be moderately phosphorylated under physiological conditions but their hyperphosphorylation reflects the pathogenicity. There are, generally, around 85 phosphorylation sites on tau but it is elusive which phosphorylation event may be the most critical step toward the pathogenicity.

Tau protein phosphorylated at threonine residue 231 (pT231-tau) is one of the hyperphosphorylated forms of tau protein which exist in the two distinct cis and trans conformation. Recent studies in mice show that cis conformation of the pT231-tau protein may be considered as a pathologic tau protein and may cause neurodegeneration upon traumatic brain injury (TBI). However, studies of exemplary embodiments of the present disclosure demonstrate that neither cis nor trans conformations of the pT231-tau proteins accumulate in human brains with Alzheimer's disease (AD). As a result, neurotoxic pT231-tau proteins in human with Alzheimer's disease may have an intermediate structure different from cis or trans conformations.

There is, therefore, a need for conformation-independent antibodies which specifically bind to neurotoxic pT231-tau proteins. There is also a need for efficient methods and kits for screening, diagnosing, and treating Alzheimer's disease using conformation-independent antibodies against neurotoxic pT231-tau proteins.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary antibody or fragment thereof capable of binding to a neurotoxic tau protein. The neurotoxic tau protein may include a phosphorylation site at threonine residue 231 in AT180 domain of tau proteins and an amino acid substitution of proline residue 232 to glycine (P232G) in AT180 domain of tau proteins. In an exemplary embodiment, the antibody or the fragment thereof may include SEQ ID NO: 1. In an exemplary embodiment, the antibody or the fragment thereof includes a heavy chain variable region (HCVR) and a light chain variable region (LCVR). In an exemplary embodiment, the heavy chain variable region (HCVR) may include heavy chain complementarity-determining regions (CDRs) with SEQ ID NOs: 2, 3, and 4. In an exemplary embodiment, the light chain variable region (LCVR) may include light chain complementarity-determining regions, the light chain CDRs may include SEQ ID NOs: 5, 6, and 7.

In an exemplary embodiment, the antibody or the fragment thereof may include SEQ ID NO: 1. In an exemplary embodiment, the antibody or the fragment thereof may include at least one of a humanized antibody or fragment thereof, a fully human humanized antibody or fragment thereof. In an exemplary embodiment, the antibody or the fragment thereof may include at least one of a chimeric antibody or fragment thereof and a recombinant antibody or fragment thereof. In an exemplary embodiment, the antibody or the fragment thereof may include at least one of a monoclonal antibody or fragment thereof and a polyclonal antibody or fragment thereof.

In an exemplary embodiment, the fragment thereof may include at least one of a single chain fragment variable (scFv), an antigen-binding fragment (Fab), and a fragment variable region (Fv). In an exemplary embodiment, the antibody or the fragment thereof may have a molecular weight between 12 kiloDaltons (kDa) and 50 kDa. In an exemplary embodiment, the antibody or the fragment thereof may be capable of binding to aggregated neurotoxic tau proteins. In an exemplary embodiment, the neurotoxic tau protein may have a conformation different from a cis conformation and trans conformation.

In another general aspect, the present disclosure describes a method for diagnosing tauopathy disorders in a subject. In an exemplary embodiment, the method may include contacting a biological sample of the subject with an antibody or fragment thereof capable of binding to a neurotoxic tau protein and detecting a tauopathy disorder in the subject responsive to formation of complexes between the neurotoxic tau protein and the antibody or the fragment thereof in the biological sample. In an exemplary embodiment, the formation of the antibody-antigen complexes may be indicative of the tauopathy disorder.

In an exemplary embodiment, the neurotoxic tau protein may be phosphorylated at threonine residue 231 and may have an amino acid substitution of P232G in AT180 domain of tau proteins. In an exemplary embodiment, the exemplary antibody or fragment thereof may be detectably labeled with a labeling agent. In an exemplary embodiment, the biological sample may include at least one of a cell, a tissue, an organ, and a fluid of the subject. In an exemplary embodiment, the tissue may include a brain tissue with neurofibrillary tangles. In an exemplary embodiment, the fluid may include at least one of cerebrospinal fluid, blood, lymph, and urine.

In an exemplary embodiment, determining the presence of the antibody-antigen complexes between the neurotoxic tau protein and the antibody or the fragment thereof may include conducting an immunoassay. In an exemplary embodiment, the immunoassay may include at least one of a radioimmunoassay, a Western blot assay, an immunofluorescent assay, an enzyme immunoassay, an immunoprecipitation assay, a chemiluminescent assay, an immunohistochemical assay, a dot blot assay, and a slot blot assay. In an exemplary embodiment, detecting the tauopathy disorder in the subject may include determining the presence of the antibody-antigen complexes using at least one of positron-emission tomography (PET) scan technique and a computerized tomography (CT) scan technique.

Other exemplary systems, methods, features, and advantages of the implementations will be or will become, apparent to one of ordinary skill in the art upon examination of the following figures and detailed description. It is intended that all such additional systems, methods, features, and advantages be included within this description and this summary, be within the scope of the implementations and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Disclosed herein is an exemplary therapeutic and diagnostic antibody or fragment thereof capable of binding to neurotoxic tau proteins. The present disclosure also relates to exemplary methods of using those antibodies for diagnostics, prevention, and treatment of tauopathy disorders. The present disclosure also describes exemplary prophylactic and therapeutic vaccines for tauopathy disorders. As used herein the "neurotoxic tau protein" may refer to pathological tau protein which may contribute to tauopathy disorders like Alzheimer's disease (AD). In an exemplary embodiment, the neurotoxic tau protein may include a phosphorylation site at threonine residue 231 (pT231-tau) in AT180 domain of tau proteins and an amino acid substitution of proline residue 232 to glycine (P232G) in AT180 domain of tau proteins. In an exemplary embodiment, the neurotoxic tau protein includes SEQ ID NO: 8.

In exemplary embodiments of the present disclosure, it may be demonstrated that neither cis nor trans conformations of the pT231-tau proteins accumulate in human brains with Alzheimer's disease (AD). Therefore, it may be concluded that conformation-independent may be required for binding to neurotoxic tau proteins with an intermediate structure different from cis or trans conformations. In an exemplary embodiment, amino acid substitution of proline residue 232 to glycine in the pT231-tau protein may allow the cis conformation and the trans conformation of the pT231-tau proteins to easily convert to each other according to bioinformatics assessments.

Figure 1:
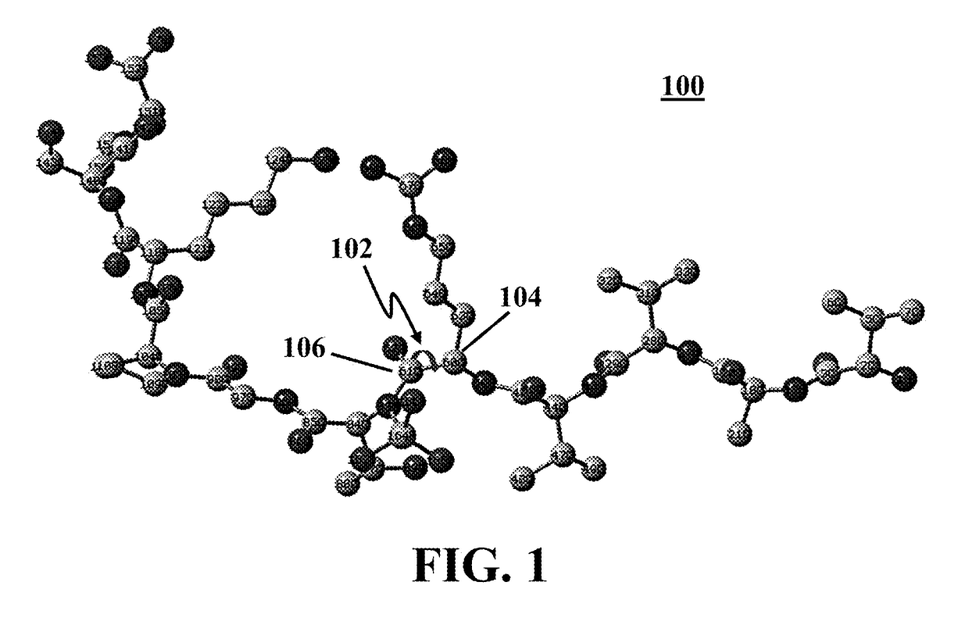
FIG. 1 shows a schematic representation of an exemplary neurotoxic tau protein phosphorylated at threonine residue 231 with an amino acid substitution of proline residue 232 to glycine (P232G) in AT180 domain of tau proteins, consistent with one or more exemplary embodiments of the present disclosure.

FIG. 1 shows a schematic representation 100 of the exemplary neurotoxic pT231-tau protein with an amino acid substitution of proline residue 232 to glycine (P232G) in AT180 domain of tau protein, consistent with one or more exemplary embodiments of the present disclosure. Referring to FIG. 1, amino acid substitution of proline residue 232 to glycine in the structure of the pT231-tau proteins may allow the pT231-tau proteins to get several conformations by rotating around C600-C610 bond 102. C600 104 is a carbon atom of threonine residue 231 and C610 106 is a carbon atom of glycine residue 232 after amino acid substitution.

In an exemplary embodiment, the exemplary antibody or fragment thereof may discriminate between neurotoxic tau proteins and normal tau proteins. In an exemplary embodiment, the exemplary antibody or fragment thereof may be capable of binding to the neurotoxic tau protein relative to normal tau protein. In an exemplary embodiment, the neurotoxic tau protein may have a conformation different from a cis conformation and trans conformation. In an exemplary embodiment, the exemplary antibody or fragment thereof may be capable of binding to aggregated neurotoxic tau protein in the biological sample.

In an exemplary embodiment, the exemplary antibody or fragment thereof may recognize the neurotoxic pT231-tau proteins irrespective to their conformations. In an exemplary embodiment, the exemplary antibody or fragment thereof may be a sequence-specific and conformation-independent antibody or fragment thereof.

In an exemplary embodiment, the antibody or the fragment thereof may include SEQ ID NO: 1. In an exemplary embodiment, the antibody or the fragment thereof includes a heavy chain variable region (HCVR) and a light chain variable region (LCVR). In an exemplary embodiment, the heavy chain variable region (HCVR) may include heavy chain complementarity-determining regions (CDRs) with SEQ ID NOs: 2, 3, and 4. In an exemplary embodiment, the light chain variable region (LCVR) may include light chain complementarity-determining regions, the light chain CDRs may include SEQ ID NOs: 5, 6, and 7.

In an exemplary embodiment, the exemplary antibody or fragment thereof may include an amino acid sequence with at least about 80%, at least about 85%, at least about 90%, at least about 95%, at least about 98%, or at least about 99% identity similar to SEQ ID NO: 1. In an exemplary embodiment, the exemplary antibody or fragment thereof may have a molecular weight between 12 kiloDaltons (kDa) and 50 kDa. In an exemplary embodiment, the exemplary fragment thereof may include at least one of a single chain fragment variable (scFv), an antigen-binding fragment (Fab), and a fragment variable region (Fv). In an exemplary embodiment, the exemplary antibody or fragment thereof may be capable of binding to aggregated neurotoxic tau proteins.

In an exemplary embodiment, the exemplary antibody or the fragment thereof may be at least one of a humanized antibody or fragment thereof, or a fully human humanized antibody or fragment thereof. In an exemplary embodiment, the exemplary antibody or the fragment thereof may be at least one of a chimeric antibody or fragment thereof and a recombinant antibody or fragment thereof. In an exemplary embodiment, the exemplary antibody or fragment thereof may be at least one of a monoclonal antibody or fragment thereof and a polyclonal antibody or fragment thereof.

In some exemplary embodiments, the exemplary antibody or fragment thereof may be produced utilizing different approaches, such as hybridoma technology and phage display biopanning technique. In an exemplary embodiment, hybridomas may be produced by fusing a suitable immortal cell line with one of a variety of antibody-producing cells, such as T cells. In an exemplary embodiment, the exemplary antibody or fragment thereof may be produced using a recombinant animal or by culturing a recombinant host cell.

In some exemplary embodiments, the exemplary antibody or fragment thereof may be used for diagnosing, preventing, or treating tauopathy disorders in a subject. In an exemplary implementation, the present disclosure describes an exemplary method for treating tauopathy disorders in a subject using the exemplary antibody or fragment thereof. The method may include administering an effective amount of the exemplary antibody or fragment thereof to the subject. In an exemplary embodiment, the exemplary method for treating tauopathy disorders in the subject may further include administering other therapeutic compounds to the subject. In an exemplary embodiment, administering the exemplary antibody or fragment thereof may elicit an immune response directed to neurotoxic tau proteins and tau deposits in the brains of patients. In an exemplary embodiment, the effective amount of the exemplary antibody or fragment thereof may be at least about 1 mg/kg body weight of the subject, per dose. In an exemplary embodiment, the effective amount of the exemplary antibody or fragment thereof may be at least about 10 mg/kg body weight of the subject, per dose.

As used herein, "tauopathy disorders" may refer to any neurodegenerative disease that involves the pathological aggregation of tau proteins within the brain. Accordingly, in addition to both familial and sporadic Alzheimer's disease, other tauopathies that may be treated using exemplary methods of the present invention include, without limitation, frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis and parkinsonism-dementia complex, dementia pugilistica, Down syndrome, GerstmannStraussler-Scheinker disease, Hallerworden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, and chronic traumatic encephalopathy.

Figure 2:
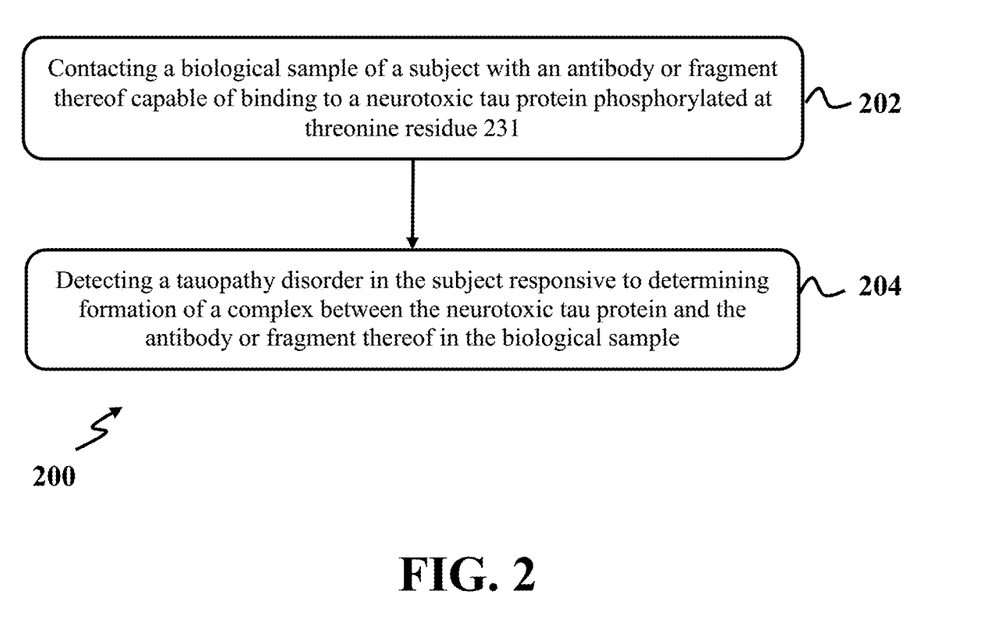
FIG. 2 shows a flowchart of a method for diagnosing and monitoring tauopathy disorders in a subject, consistent with one or more exemplary embodiments of the present disclosure.

FIG. 2 shows a flowchart of an exemplary method 200 in which the exemplary antibody or fragment thereof of the present disclosure may be employed for diagnosing and monitoring tauopathy disorders in a subject, consistent with one or more exemplary embodiments of the present disclosure. An exemplary method 200 may include contacting a biological sample of the subject with the exemplary antibody or fragment thereof capable of binding to a neurotoxic tau protein (step 202) and detecting a tauopathy disorder in the subject responsive to formation of a complex between neurotoxic tau proteins of the biological sample and the exemplary antibody or fragment thereof (step 204).

In further detail with respect to step 202, in an exemplary embodiment, the antibody or fragment thereof may bind to neurotoxic tau proteins irrespective to their conformation. Therefore, if the biological sample of the subject contains neurotoxic tau protein, antibody-antigen complexes may be formed between the antibody or fragment thereof and the neurotoxic tau proteins upon contacting the biological sample of the subject with the exemplary antibody or fragment thereof. In an exemplary embodiment, the neurotoxic tau proteins may be phosphorylated at threonine residue 231 and may have an amino acid substitution of proline to glycine at residue 232.

In an exemplary embodiment, contacting the biological sample of the subject with the exemplary antibody or fragment thereof may include contacting the biological sample of the subject with the exemplary antibody or fragment thereof under conditions enabling formation of complexes between the exemplary antibodies or fragment thereof and the neurotoxic tau proteins (hereinafter named as "antibody-antigen complexes").

In an exemplary embodiment, contacting may refer to putting in contact two or different materials or matters.

In an exemplary embodiment, the exemplary antibody or fragment thereof may be detectably labeled with a labeling agent. In an exemplary embodiment, the labeling agent may include at least one of an enzyme, a radioisotope, a fluorophore, a nuclear magnetic resonance marker, and a heavy metal. In an exemplary embodiment, the biological sample may include at least one of a cell, a tissue, an organ, and fluid of the subject. In an exemplary embodiment, the tissue may include brain tissue with neurofibrillary tangles. In an exemplary embodiment, the brain tissue may include at least one of a hippocampal tissue and a frontal cortex tissue. In an exemplary embodiment, the fluid may include at least one of cerebrospinal fluid, blood, lymph, and urine.

In further detail with respect to step 204, in an exemplary embodiment, detecting the tauopathy disorder in the subject may include determining a presence of the complexes between the neurotoxic tau protein and the antibody or the fragment thereof (antibody-antigen complexes) in the biological sample. In an exemplary embodiment, presence and/or amount of antibody-antigen complexes may be determined by methods known in the art. In an exemplary embodiment, the presence of the complexes may be indicative of the tauopathy disorder in the subject. In an exemplary embodiment, a significantly higher amount of antibody-antigen complexes in the biological sample of the subject than a control sample indicating the presence of a tauopathy disorder in the subject.

In an exemplary embodiment, determining the presence of the complexes between the neurotoxic tau protein and the antibody or the fragment thereof may include conducting an immunoassay. In an exemplary embodiment, the immunoassay may include at least one of a radioimmunoassay, a Western blot assay, an immunofluorescent assay, an enzyme immunoassay, an immunoprecipitation assay, a chemiluminescent assay, an immunohistochemical assay, a dot blot assay, and a slot blot assay. In an exemplary embodiment, surface plasmon resonance (SPR) technique may be used to determine antibody-antigen complexes by direct monitoring of binding event of the exemplary antibody or fragment thereof to neurotoxic tau proteins in real time.

In an exemplary embodiment, the exemplary antibody or fragment thereof may be used for monitoring a subject for the presence, progression, regression, or stabilization of Alzheimer's disease or related tauopathies, or for determining the stage of Alzheimer's disease or other tauopathies disorders in a subject. In an exemplary embodiment, the exemplary antibody or fragment thereof may be administered intravenously, intramuscularly, subcutaneously, intraperitoneally, intranasally, intracerebroventricularly, intrathecally, or as an aerosol for monitoring the tauopathy disorder.

In an exemplary embodiment, the exemplary antibody or fragment thereof may be radiolabeled. In an exemplary embodiment, upon administering an exemplary radiolabeled antibody or fragment thereof to the subject, the exemplary radiolabeled antibody or fragment thereof may distinguish between normal (physiological) and neurotoxic (pathological) tau proteins and may form antibody-antigen complexes with the neurotoxic tau proteins. Therefore, the presence of the antibody-antigen complexes may be determined using in-vivo imaging techniques, such as positron emission tomography (PET) scan and computerized tomography (CT) scan.

In an exemplary implementation, the present disclosure may be further directed to an exemplary kit (not illustrated) for performing the above described diagnostic method 200 and the monitoring method. In an exemplary embodiment, the exemplary kit may include the exemplary antibody or fragment thereof as a diagnostic reagent which has antigenic specificity for neurotoxic tau proteins phosphorylated at threonine residue 231 (pT231-tau) with an amino acid substitution of proline residue 232 to glycine (P232G) in AT180 domain of tau proteins. In an exemplary embodiment, the exemplary kit may further include a detectable label.

In an exemplary embodiment, the exemplary antibody or fragment thereof may contain a detectable label, such as fluorescent molecule and biotin, which is directly detectable or detectable via a secondary reaction, such as a reaction with streptavidin. Alternatively, a second reagent containing the detectable label may be utilized, where the second reagent may have binding specificity to the primary antibody.

In an exemplary implementation, the present disclosure also describes exemplary therapeutic and prophylactic vaccine compositions to confer passive immunity against tauopathy disorders to a subject. In an exemplary embodiment, the vaccine compositions may include the exemplary antibody or fragment thereof of the present disclosure. In an exemplary embodiment, prophylactic vaccines may be used to reduce the likelihood of a subject acquiring a tauopathy disorder, such as Alzheimer's disease. In an exemplary embodiment, therapeutic vaccines may be used to treat subjects diagnosed with a tauopathy disorder. In one embodiment, the vaccine composition may include an exemplary antibody or fragment thereof that binds to the neurotoxic tau proteins phosphorylated at threonine residue 231 (pT231-tau) with an amino acid substitution of proline residue 232 to glycine (P232G) in AT180 domain of tau proteins. In an exemplary embodiment, the therapeutic vaccine compositions may further include at least one therapeutic compound.

In an exemplary embodiment, the therapeutic and prophylactic vaccine compositions may further include an adjuvant, such as a cytokine, a lymphokine, and a chemokine. In an exemplary embodiment, the chemokine may further include interleukin-2 (IL-2), granulocyte-macrophage-colony-stimulating factor (GM-CSF), interleukin-12 (IL-12), γ-interferon, IP-10, MIP1β, and chemokine ligand 5 (CCL5). As used herein, "adjuvant" refers to one or more substances that cause stimulation of the immune system. In this context, an adjuvant may be used to enhance an immune response to one or more vaccine antigens or antibodies. An adjuvant may be administered to a subject before, in combination with, or after administration of the vaccine. Examples of chemical compounds used as adjuvants may include at least one of aluminum compounds, oils, block polymers, immune stimulating complexes, vitamins and minerals (e.g., vitamin E, vitamin A, selenium, and vitamin B12), saponins, and bacterial and fungal cell wall components.

EXAMPLES

Example 1: Producing the Exemplary Antibody Against the Neurotoxic Tau Protein In this example, the exemplary antibody was produced using the phage display biopanning technique, in which the neurotoxic tau protein including SEQ ID NO: 8 was immobilized to a surface and a human single-chain variable fragment (scFv) antibody library was applied to the immobilized neurotoxic tau proteins for identifying the antibody bound the neurotoxic tau protein (hereinafter called "bound antibodies"). Finally, one or more high-affinity antibodies against the neurotoxic tau protein were selected among the bound antibodies.

At first, in order to produce a phage library, pegylated M13K07 with a concentration of about $10^{13}$ phage/ml were produced as a helper phage. Phage library re-amplification was done and the phage library was stored at a temperature of about −80° C. in 20 aliquots. The Titer of phage stock was about $8.6 \times 10^{12}$ in 1 ml after amplification. In the next step, panning of the phage stock was accomplished in 4 rounds against the immobilized neurotoxic tau protein. Then, a washing step was done to remove away unbound phages. Afterward, bound phages displaying high-affinity scFv against the neurotoxic tau protein were eluted for further analysis. In the end, 7 antibodies were selected as high-affinity antibodies against the neurotoxic tau protein. Also, an enzyme-linked immunosorbent assay (ELISA) assay was also conducted to determine the binding specificity of the exemplary antibody clones of the present disclosure to the neurotoxic pT231-tau proteins as an antigen.

Figure 3:
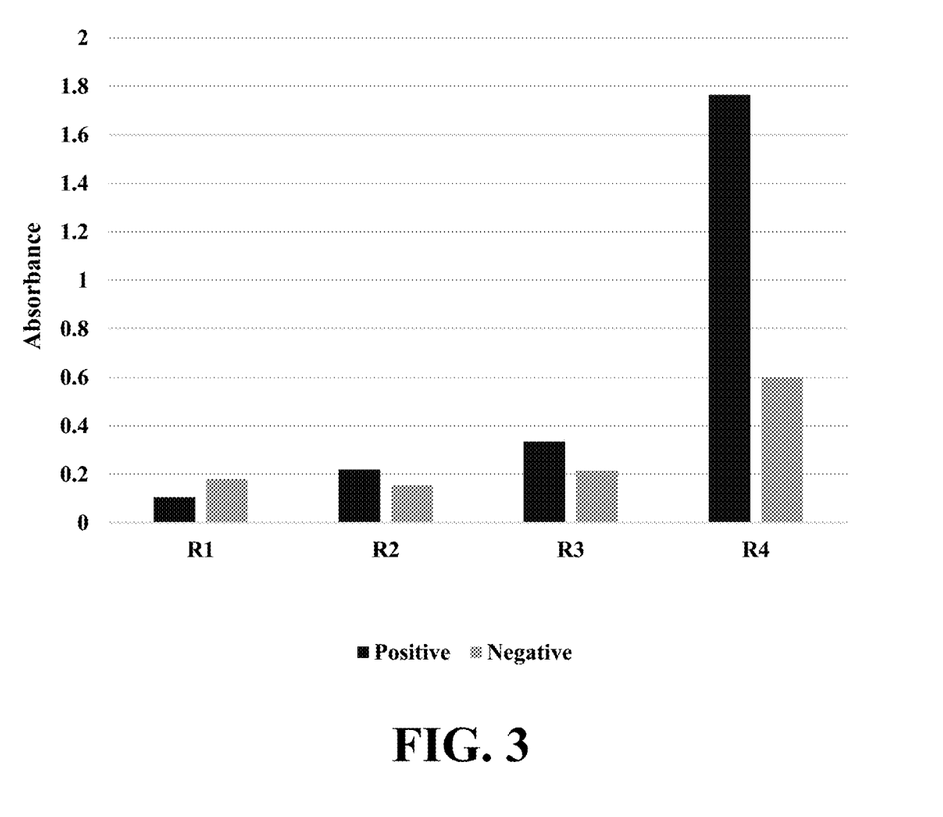
FIG. 3 shows enrichment of the specific exemplary antibody clones bound to a neurotoxic pT231-tau antigenic peptide, consistent with one or more exemplary embodiments of the present disclosure.

FIG. 3 shows enrichment of the specific exemplary antibody clones bound to the neurotoxic pT231-tau antigenic peptide, consistent with one or more exemplary embodiments of the present disclosure. Referring to FIG. 3, according to absorbance data of each group, there has been an enrichment in clone bound to the exemplary pT231-tau antigenic peptide upon 4 rounds of biopanning. As a result, phages of round 4 were used for the production of monoclonal antibodies.

In the next step, an exemplary scFv antibody including a His tag was expressed using selected bacterial clones and purified. Shortly, a single colony expressing each scFv antibody was grown in 10 mL culture media (ampicillin) at a temperature of about 37° C. for overnight. The overnight culture was diluted 1:100 in 400 ml of media and grown at a temperature of about 37° C. to reach an optical density of about 0.9 at a wavelength of about 600 nm ($OD_{600}$). After that, Isopropyl β-D-1-thiogalactopyranoside (IPTG) with a concentration of about 1 mM was added for periplasmic fraction extraction. Then, the bacterial culture was harvested and resuspended in 1:20 of the culture volume of ice-cold lysis buffer. Following 30 min incubation, the periplasmic fraction containing the antibody fragment was collected by centrifuging at a velocity of about 20000 g at a temperature of about 4° C. for a time period of about 30 minutes. The periplasmic fraction containing the antibody fragments was dialyzed for overnight. In the end, His-tagged antibody fragments were purified by using Talon cobalt resin. Expression and purification processes were confirmed by sodium dodecyl sulfate-polyacrylamide gel electrophoresis (SDS-PAGE) and Western blotting.

Example 2: Investigating the Presence of the Neurotoxic Tau Protein in Post-Mortem Brains with Alzheimer's Diseases In this example, the presence of the neurotoxic tau proteins and their conformation in post-mortem brains of those patients with Alzheimer's disease were assessed. At first, tissue samples of post-mortem brains of a healthy subject and a patient with Alzheimer's disease were stained by cis and trans pT231-tau antibodies and isotype-specific secondary antibodies.

Figure 4:
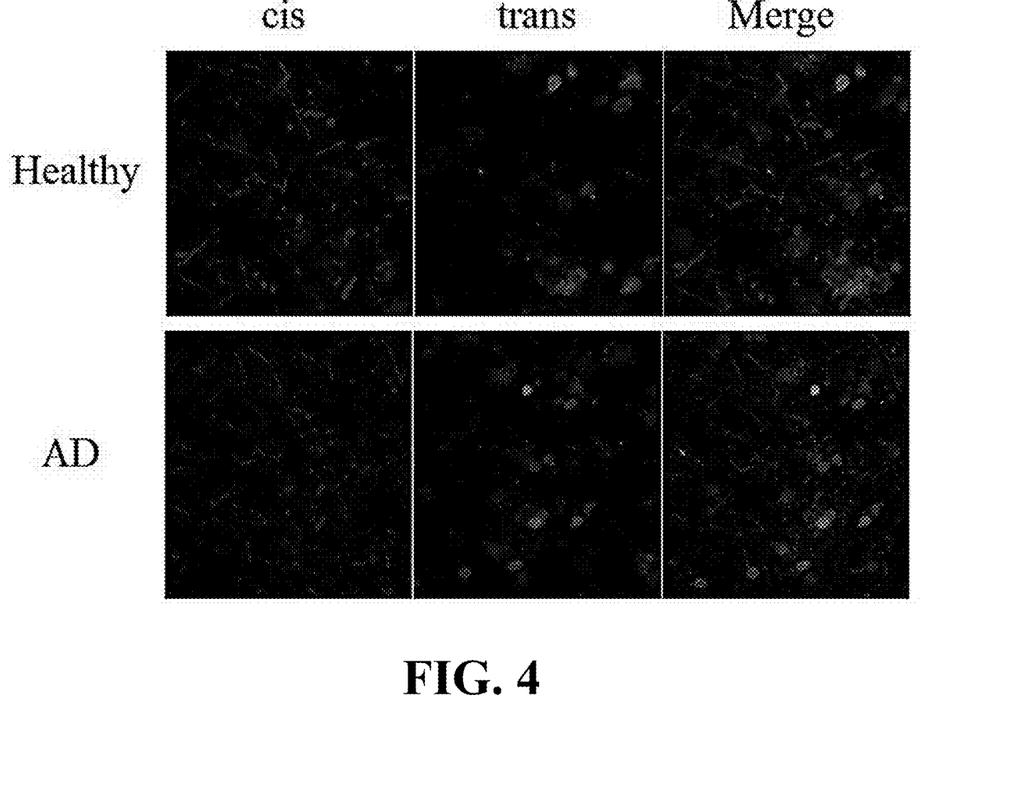
FIG. 4 shows immunofluorescent images of cis and trans conformations of phosphorylated tau proteins in post-mortem brains of a healthy subject and a patient with Alzheimer's disease, consistent with one or more exemplary embodiments of the present disclosure.

FIG. 4 shows immunofluorescent images of cis and trans conformations of phosphorylated tau proteins in post-mortem brains of a healthy subject and a patient with Alzheimer's disease, consistent with one or more exemplary embodiments of the present disclosure. Referring to FIG. 4, there was no difference between immunofluorescent (IF) intensity of the control healthy subjects and the AD brains, and the IF intensity of both groups was about 3500000 for all groups. Therefore, there is no accumulation of cis and trans conformations of tau proteins phosphorylated at threonine residue 231 (pT231-tau proteins) in Alzheimer's disease (AD) brain compared to healthy subjects.

Figure 5A:
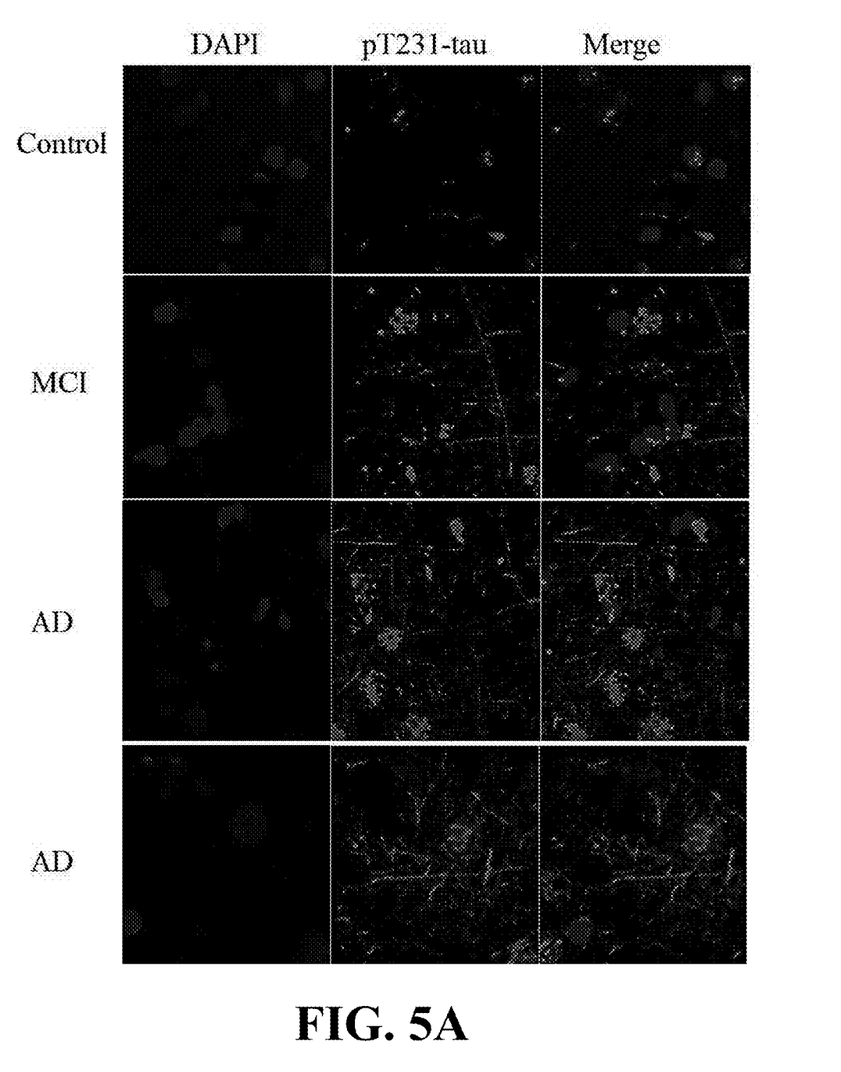
FIG. 5A shows immunofluorescent images of tissue samples of post-mortem brains of a healthy subject, a patient with mild cognitive impairment (MCI), and two patients with Alzheimer's disease stained with the exemplary antibody with SEQ ID NO: 1, consistent with one or more exemplary embodiments of the present disclosure.
Figure 5B:
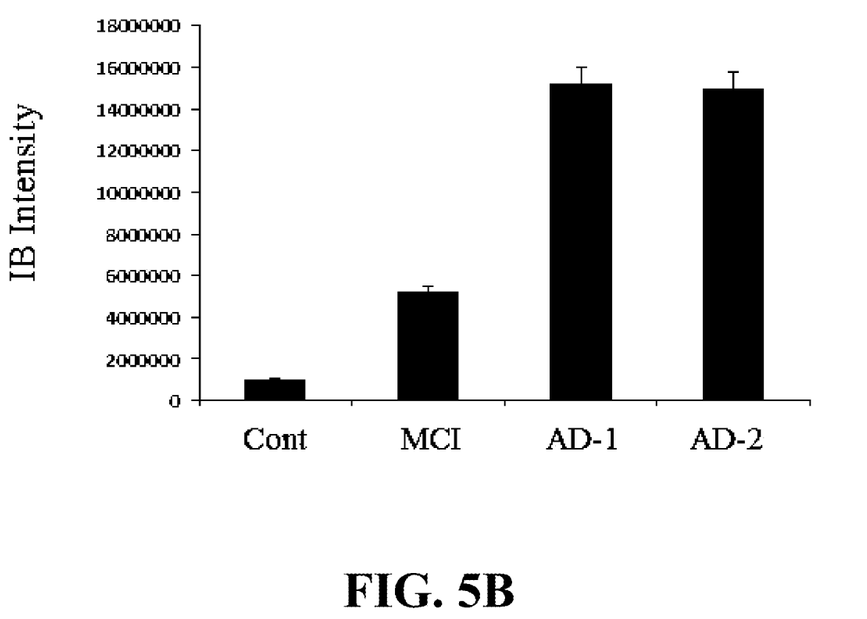
FIG. 5B shows immunofluorescent intensities of post-mortem brains of a healthy subject (cont), a patient with mild cognitive impairment (MCI), and two patients with Alzheimer's disease (AD-1 and AD-2) stained with the exemplary antibody of the present disclosure, consistent with one or more exemplary embodiments of the present disclosure.

Furthermore, in order to validate an increase of the neurotoxic tau protein in Alzheimer's disease, tissue samples of post-mortem brains of a healthy subject, a patients with mild cognitive impairment (MCI), and two patients with Alzheimer's disease were stained using the exemplary antibody of the present disclosure with SEQ ID NO: 1. FIG. 5A shows immunofluorescent images of tissue samples of post-mortem brains of a healthy subject, a patient with mild cognitive impairment (MCI), and two patients with Alzheimer's disease stained with the exemplary antibody with SEQ ID NO: 1, consistent with one or more exemplary embodiments of the present disclosure. FIG. 5B shows the immunofluorescent intensities of post-mortem brains of a healthy subject (cont), a patient with mild cognitive impairment (MCI), and two patients with Alzheimer's disease (AD-1 and AD-2) stained with the exemplary antibody of the present disclosure, consistent with one or more exemplary embodiments of the present disclosure.

There is a gradual neuron loss in Alzheimer's disease nominated by several stages. It has been demonstrated that mild cognitive impairment (MCI) primes later stages AD and shows lesser neurodegeneration compared to more developed AD. Therefore, it may be assumed that there is also a gradual increase in neurotoxic tau as the AD develops. Referring to FIGS. 5A and 5B, immunofluorescence intensities in tissue samples of post-mortem brains of a patient with mild cognitive impairment (MCI) and two patients with Alzheimer's disease are significantly higher than the control group. Also, fluorescence intensities in tissue samples of post-mortem brains of two patients with Alzheimer's disease are higher than a patient with mild cognitive impairment (MCI). Therefore, the neurotoxic tau proteins diffuse into neurites and profoundly accumulated in post-mortem human brains with Alzheimer's disease.

It may be concluded that while the exemplary antibody with SEQ ID NO: 1 is capable of recognizing the neurotoxic tau proteins in post-mortem brains of those patients with Alzheimer's disease, this exemplary antibody with SEQ ID NO: 1 may potentially have several applications for suppressing and neutralizing neurotoxic tau proteins in brain neurons of patients with Alzheimer's disease.

Figure 6A:
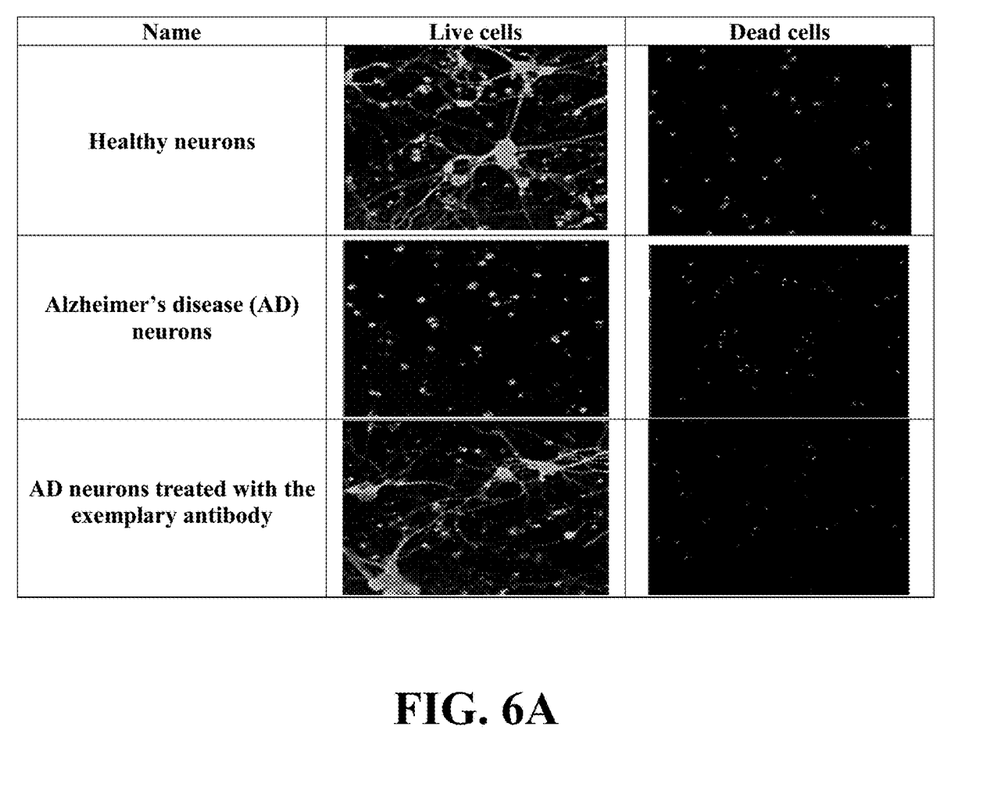
FIG. 6A shows immunofluorescent images of live cells and dead cells in healthy neurons, Alzheimer's disease (AD) neurons, and AD neurons treated with the exemplary antibody, consistent with one or more exemplary embodiments of the present disclosure.
Figure 6B:
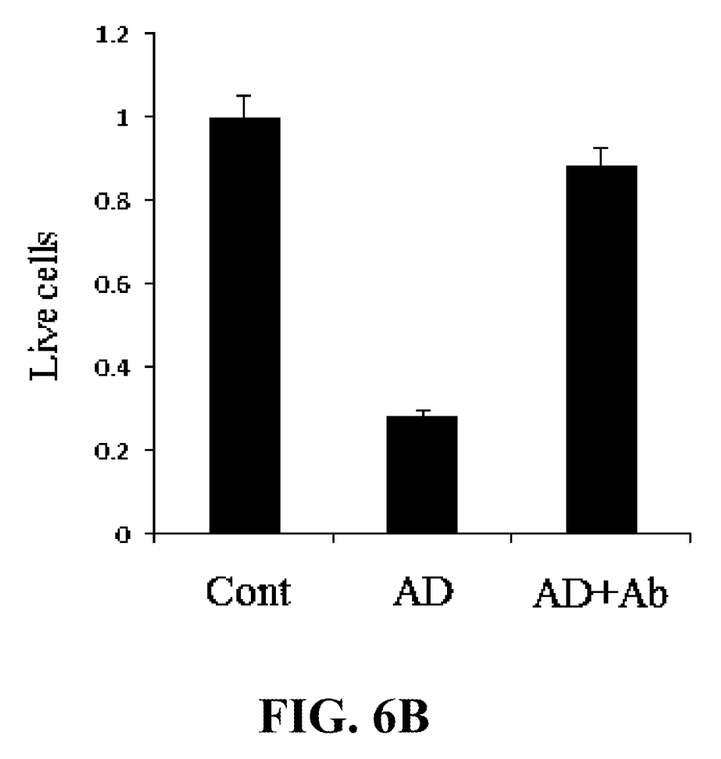
FIG. 6B shows a percentage of live cells in cultured healthy neurons, cultured Alzheimer's disease (AD) neurons, and cultured AD neurons treated with the exemplary antibody, consistent with one or more exemplary embodiments of the present disclosure.

Example 3: In-Vitro Assessment of the Exemplary Antibody Against for Suppressing Neurodegeneration In this example, in-vitro assessment of the exemplary antibody with SEQ ID NO: 1 was done by investigating neurodegeneration of cultured neurons generated from healthy human induced pluripotent stem cells (iPSCs), cultured Alzheimer's disease (AD) neurons, and cultured AD neurons treated with the exemplary antibody with SEQ ID NO: 1. FIG. 6A shows immunofluorescent images of live cells and dead cells in cultured healthy neurons, Alzheimer's disease (AD) neurons, and AD neurons treated with the exemplary antibody, consistent with one or more exemplary embodiments of the present disclosure. FIG. 6B shows a percentage of live cells in cultured healthy neurons (cont), cultured Alzheimer's disease neurons (AD), and cultured AD neurons treated with the exemplary antibody (AD+Ab), consistent with one or more exemplary embodiments of the present disclosure.

Referring to FIGS. 6A and 6B, there has been a suppressed neurodegeneration in the cultured AD neurons treated with the exemplary antibody (AD+Ab) compared to the cultured Alzheimer's disease neurons (AD).

Example 4: Molecular Modeling of the Neurotoxic Tau Protein

In this example, possible conformers of the exemplary neurotoxic pT231-tau protein with an amino acid substitution of proline residue 232 to glycine (P232G) were predicted using molecular modeling. Possible conformers which are produced by rotation about single bonds in the vicinity of $PO_3H_2$ group were predicted using molecular modeling based on density functional theory (DFT). The generalized gradient approximation (GGA) with Perdew-Burke-Ernzerhof (PBE) parameterization was also applied to describe the exchange-correlation interaction.

Figure 7A:
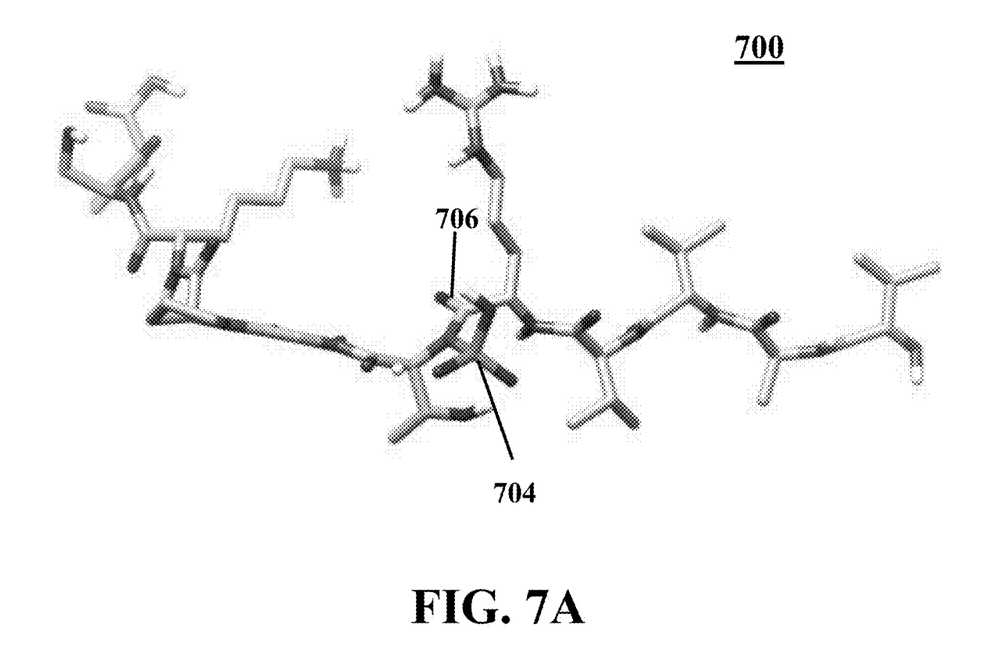
FIG. 7A shows an exemplary conformer of the exemplary neurotoxic tau protein with a total energy of about −4360.3024381 Ha, consistent with one or more exemplary embodiments of the present disclosure.
Figure 7B:
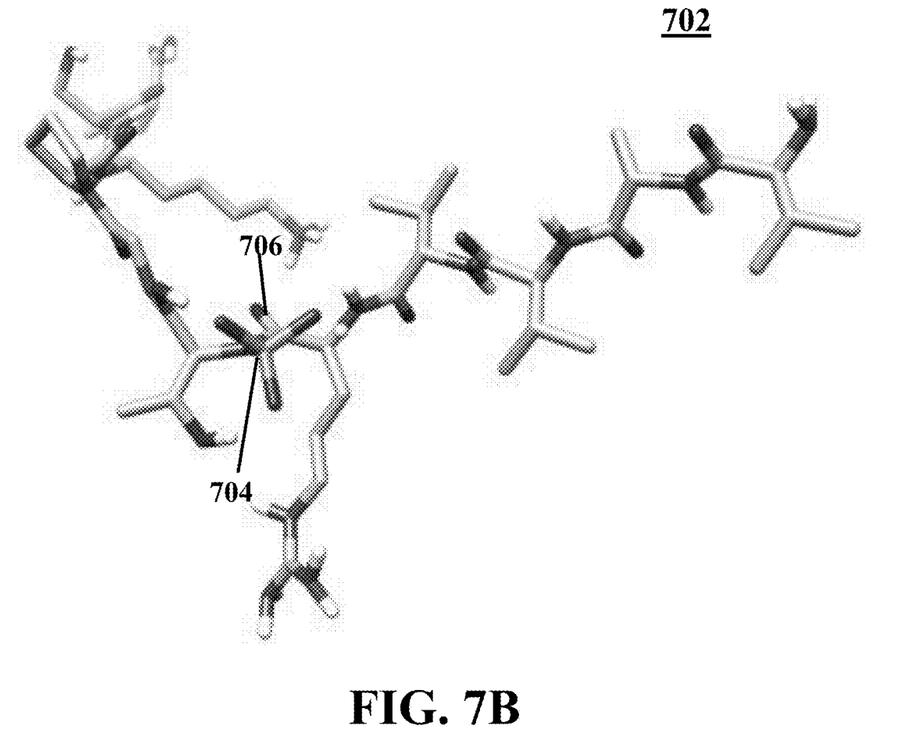
FIG. 7B shows an exemplary conformer of the exemplary neurotoxic tau protein with a total energy of about −4360.3092063 Ha, consistent with one or more exemplary embodiments of the present disclosure.

Also, the conformers were fully optimized with a convergence criterion of 0.02 Ha Å-1. The convergence tolerance of energy set to $1.0e^{-4}$ Ha. According to the molecular modeling, the exemplary neurotoxic tau protein has two conformers with total energies of about −4360.3024381 Ha and about −4360.3092063 Ha. FIG. 7A shows an exemplary conformer of the exemplary neurotoxic tau protein with a total energy of about −4360.3024381 Ha, consistent with one or more exemplary embodiments of the present disclosure. FIG. 7B shows an exemplary conformer of the exemplary neurotoxic tau protein with a total energy of about −4360.3092063 Ha, consistent with one or more exemplary embodiments of the present disclosure. According to FIGS. 7A and 7B, 704 is the threonine residue 231 and 706 is the glycine residue 232.

Referring to FIGS. 7A and 7B, energy analysis of the conformers revealed that the conformer 702 of FIG. 7B is more stable than conformer 700 of FIG. 7A. Furthermore, the low energy barrier between the two conformers, which is approximately $6.8 \times 10^{-3}$ Ha (4.25 kcal/mol), may permit conversion of each conformer into each other at room temperature. Therefore, the conformation of the exemplary neurotoxic tau protein changes easily and the exemplary neurotoxic tau protein does not have a fixed cis or trans conformation.

In an exemplary embodiment, the examples are consistent with method 200 and the details may be employed while implementing method 200.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. An antibody or fragment thereof capable of binding to a neurotoxic tau protein, the antibody or fragment thereof comprises:
   a heavy chain variable region (HCVR) comprising heavy chain complementarity-determining regions (CDRs), the heavy chain CDRs comprises SEQ ID NOs: 2, 3, and 4; and
   a light chain variable region (LCVR) comprising light chain complementarity-determining regions, the light chain CDRs comprises SEQ ID NOs: 5, 6, and 7.

2. The antibody or fragment thereof of claim 1, wherein the antibody or fragment thereof is one of a humanized antibody or fragment thereof and a human antibody or fragment thereof.

3. The antibody or the fragment thereof of claim 1, wherein the antibody or fragment thereof is one of a chimeric antibody or fragment thereof and a recombinant antibody or fragment thereof.

4. The antibody or the fragment thereof of claim 1, wherein the antibody or the fragment thereof is one of a monoclonal antibody or fragment thereof and a polyclonal antibody or fragment thereof.

5. The antibody or the fragment thereof of claim 1, wherein the fragment thereof is one of a single chain fragment variable (scFv), an antigen-binding fragment (Fab), and a fragment variable region (Fv).

6. The antibody or the fragment thereof of claim 1, wherein the antibody or the fragment thereof has a molecular weight between 12 kiloDaltons (kDa) and 50 kDa.

7. An antibody or fragment thereof capable of binding to a neurotoxic tau protein,
   wherein the neurotoxic tau protein comprises:
      a phosphorylation site at threonine residue 231 in AT180 domain of tau proteins; and
      an amino acid substitution of proline residue 232 to glycine (P232G) in AT180 domain of tau proteins, and
   wherein the antibody or fragment thereof comprises SEQ ID NO: 1.

8. A method for diagnosing tauopathy disorders in a subject, the method comprising:
   contacting a biological sample of the subject with an antibody or fragment thereof capable of binding to a neurotoxic tau protein phosphorylated at threonine residue 231, the neurotoxic tau protein comprising an amino acid substitution of P232G in AT180 domain of tau proteins; and
   detecting a tauopathy disorder in the subject responsive to formation of a complex between the neurotoxic tau protein and the antibody or the fragment thereof in the biological sample,
wherein the formation of the complex is indicative of the tauopathy disorder, and wherein the antibody or the fragment thereof comprises:
   a heavy chain variable region (HCVR), comprising heavy chain complementarity-determining regions (CDRs), the heavy chain CDRs comprises SEQ ID NOs: 2, 3, and 4; and
   a light chain variable region (LCVR), comprising light chain complementarity-determining regions, the light chain CDRs comprises SEQ ID NOs: 5, 6, and 7.

9. The method of claim 8, wherein the antibody or the fragment thereof comprises a labeling agent.

10. The method of claim 8, wherein contacting the biological sample of the subject with the antibody or the fragment thereof capable of binding to the neurotoxic tau protein phosphorylated at threonine residue 231 comprises contacting the biological sample of the subject with the antibody or the fragment thereof in an immunoassay selected from the group consisting of a radioimmunoassay, a Western blot assay, an immunofluorescent assay, an enzyme immunoassay, an immunoprecipitation assay, a chemiluminescent assay, an immunohistochemical assay, a dot blot assay, and a slot blot assay.

11. The method of claim 8, wherein detecting the tauopathy disorder in the subject comprises determining the formation of the complex between the neurotoxic tau protein and the antibody or the fragment thereof using at least one of positron-emission tomography (PET) scan technique and computerized tomography (CT) scan technique.

12. The method of claim 8, wherein the biological sample comprises at least one of a cell, tissue, organ, and fluid of the subject.

13. The method of claim 12, wherein the tissue comprises brain tissue including neurofibrillary tangles.

14. The method of claim 12, wherein the fluid comprises at least one of cerebrospinal fluid, blood, lymph, and urine.

15. A method for diagnosing tauopathy disorders in a subject, the method comprising:
   contacting a biological sample of the subject with an antibody or fragment thereof capable of binding to a neurotoxic tau protein phosphorylated at threonine residue 231, the neurotoxic tau protein comprising an amino acid substitution of P232G in AT180 domain of tau proteins; and
   detecting a tauopathy disorder in the subject responsive to formation of a complex between the neurotoxic tau protein and the antibody or the fragment thereof in the biological sample,
   wherein the formation of the complex is indicative of the tauopathy disorder, and wherein the antibody or the fragment thereof comprises SEQ ID NO: 1.

* * * * *